United States Patent
Hozumi et al.

(10) Patent No.: US 6,806,243 B2
(45) Date of Patent: Oct. 19, 2004

(54) OPHTHALMIC SOLUTION AND CONTACT LENS SOLUTION

(75) Inventors: Kentaro Hozumi, Rockville, MD (US); Osamu Mori, Kasugai (JP); Akira Tsuzuki, Nagoya (JP)

(73) Assignee: Menicon Co., Ltd., Nagoya (JP)

( * ) Notice: Subject to any disclaimer, the term of this patent is extended or adjusted under 35 U.S.C. 154(b) by 204 days.

(21) Appl. No.: 10/244,690

(22) Filed: Sep. 16, 2002

(65) Prior Publication Data

US 2003/0153622 A1 Aug. 14, 2003

(30) Foreign Application Priority Data

Sep. 17, 2001 (JP) ........................................ 2001-281471
Aug. 1, 2002 (JP) ........................................ 2002-224761

(51) Int. Cl.[7] ................................................ C11D 3/48
(52) U.S. Cl. ...................... 510/112; 510/384; 510/488; 510/499
(58) Field of Search ................................ 510/112, 384, 510/488, 499

(56) References Cited

U.S. PATENT DOCUMENTS

| | | | |
|---|---|---|---|
| 4,087,538 A | * | 5/1978 | Portnoff ........................ 514/420 |
| 4,136,173 A | * | 1/1979 | Pramoda et al. ............... 514/15 |
| 4,425,346 A | * | 1/1984 | Horlington .................... 514/249 |
| 4,470,965 A | * | 9/1984 | Wolf et al. .................... 514/652 |
| 4,758,595 A | | 7/1988 | Ogunbiyi et al. |
| 4,836,986 A | | 6/1989 | Ogunbiyi et al. |
| 4,863,900 A | * | 9/1989 | Pollock et al. ................ 514/12 |
| 5,556,848 A | * | 9/1996 | Kimura et al. ................ 514/179 |
| 5,658,948 A | | 8/1997 | Lucero |
| 5,741,817 A | * | 4/1998 | Chowhan et al. ............. 514/561 |
| 5,770,596 A | * | 6/1998 | Coquelet et al. ............. 514/225.2 |
| 5,886,030 A | * | 3/1999 | Maniar ......................... 514/458 |
| 5,916,550 A | * | 6/1999 | Inada et al. ................... 424/78.04 |
| 5,998,488 A | * | 12/1999 | Shinohara et al. ............ 424/658 |
| 6,231,889 B1 | * | 5/2001 | Richardson et al. .......... 424/464 |
| 6,583,181 B1 | * | 6/2003 | Chiang et al. ................ 514/642 |

FOREIGN PATENT DOCUMENTS

| | | |
|---|---|---|
| EP | 0 055 515 A2 | 7/1982 |
| EP | 0 701 821 A1 | 3/1996 |
| JP | 4-231054 | 8/1992 |
| JP | 2550036 | 10/1996 |
| JP | 8-512145 | 12/1996 |
| JP | 10-108899 | 4/1998 |
| JP | 11-249087 | 9/1999 |
| WO | 90/02555 A | 3/1990 |
| WO | 95/30414 | * 11/1995 |
| WO | 95/30414 A | 11/1995 |
| WO | 96/03158 A | 2/1996 |

* cited by examiner

*Primary Examiner*—Charles Boyer
(74) *Attorney, Agent, or Firm*—Burr & Brown

(57) ABSTRACT

An ophthalmic solution or contact lens solution comprising at least one germicidal/preservative component. The ophthalmic solution further comprises at least one selected amino-acid-based component, 0–0.2 wt. % of sodium chloride, and 0–0.5 wt. % of phosphate. The contact lens solution further comprises at least one selected acidic component and 0–0.2 wt. % of sodium chloride. Alternatively, the contact lens solution further comprises at least one selected amino-acid-based component, at least one selected acidic compound, and 0–0.2 wt. % of sodium chloride.

21 Claims, No Drawings

OPHTHALMIC SOLUTION AND CONTACT LENS SOLUTION

This application is based on Japanese Patent Applications Nos. 2001-281471 filed on Sep. 17, 2001 and 2002-224761 filed on Aug. 1, 2002, the contents of which are incorporated hereinto by reference.

BACKGROUND OF THE INVENTION

1. Field of the Invention

The present invention relates in general to an ophthalmic solution and a solution for a contact lens. In particular, the invention is concerned with such a solution used as a contact lens sterilizing or germicidal solution, a contact lens sterilizing and cleaning solution, a contact lens sterilizing and storing solution, a contact lens sterilizing, cleaning, and storing solution, a contact lens cleaning and/or storing solution, a collyrium or eye drops, or a preservative in cosmetics. More specifically, the invention is concerned with such a solution which exhibits an excellent germicidal (or sterilizing) or preservative effect or assures excellent compatibility with the contact lens without causing a change of the size of the contact lens, while exhibiting a sufficiently high degree of safety to the eye and the skin of the user.

2. Discussion of the Related Art

A solution for a contact lens (hereinafter referred to as "contact lens solution") contains a germicidal or preservative component to prevent contamination of the contact lens by molds and microorganisms such as bacteria, in addition to a cleaning component to remove deposits adhering to the contact lens such as protein and lipid which derive from tear fluid and lipid of the eye.

Although various compounds are conventionally proposed as the germicidal component contained in the contact lens solution (contact lens sterilizing solution), it is necessary to use those compounds in relatively high concentrations for permitting the solution to exhibit practically sufficient germicidal characteristics. For instance, biguamide compounds whose typical example is polyhexamethylene biguamide (PHMB) as an organic nitrogen germicide and quaternary ammonium compounds whose typical examples are benzalkonium chloride and polyquaternium have been widely used as the germicidal component included in the contact lens solution since the biguamide compounds and the quaternary ammonium compounds exhibit particularly effective germicidal characteristics superior to those of conventional germicidal components. A recent study, however, reveals that the biguamide compounds or the quaternary ammonium compounds alone do not provide a sufficiently high degree of germicidal or preservative effect unless those compounds are used in relatively high concentrations.

For assuring a practically useful germicidal or preservative effect, it is necessary to increase the amount of the germicidal component to be included in the contact lens solution. The biguamide compounds or the quaternary ammonium compounds if used in high concentrations, however, are toxic to the eye, and likely to be adsorbed on the contact lens, especially the soft contact lens. In this case, the germicidal component undesirably may irritate the mucous membranes of the eye to cause trouble with the eye, giving rise to a problem of insufficient safety. In view of this, various studies have been made to provide a contact lens solution capable of exhibiting a higher germicidal effect while reducing the required amount of the germicidal component.

For instance, JP-A-10-108899 discloses a contact lens solution which assures safety to the eye while exhibiting an excellent germicidal effect. In the disclosed solution, the polyhexamethylene biguamide as the biguamide germicide is used in combination with a nonionic tonicity adjusting agent such as glycerin or propylene glycol. JP-A-11-249087 discloses a contact lens solution which assures safety to the eye while exhibiting an excellent disinfecting effect. In the disclosed solution, the polyquaternium is used in combination with the nonionic tonicity adjusting agent and/or amino acid. Although the germicidal efficacy of each of the disclosed contact lens solutions is improved to some extent owing to the combined use of the compounds described above, there is still room for improvement in the characteristics of the solutions.

Even if the germicidal component such as the polyhexamethylene biguamide or the polyquaternium is used in low concentrations, the germicidal component which adheres to or is adsorbed on the contact lens may cause various troubles with the user's eye, such as inflammation of the eye and staining of the cornea over the substantially entire surface with fluorescein. The staining of the cornea with the fluorescein indicates that the cornea suffers from some trouble such as a wound or an ulcer. Depending upon the kind of the nonionic tonicity adjusting agent and/or the amino acid to be used in combination with the germicidal component, the size of the contact lens may be undesirably changed, in other words, the contact lens may suffer from swelling or shrinkage, resulting in an undesirable change of the specifications of the contact lens.

SUMMARY OF THE INVENTION

The present invention was developed in the light of the background art situations described above. It is therefore a first object of the present invention to provide an ophthalmic solution and a solution for a contact lens, which assure an excellent germicidal or preservative effect while assuring a sufficiently high degree of safety to a living subject or body (human body) by minimizing toxicity to the living subject.

It is a second object of the invention to provide a solution for a contact lens which assures a considerably high degree of safety to the eye of the contact lens user by inhibiting adhesion and adsorption of the germicidal or preservative component to and on the contact lens.

It is a third object of the invention to provide a solution for a contact lens which prevents swelling or shrinkage of the contact lens so as not to cause a change of the size of the contact lens and which assures excellent compatibility with the contact lens.

An extensive study made by the inventors of the present invention to attain the above-indicated first object has revealed that the germicidal activity exhibited by the biguamide germicide or the quaternary ammonium salt germicide included in the ophthalmic solution is inhibited by an electrolyte such as sodium chloride generally included in the solution for adjusting its osmotic pressure, or an inorganic salt buffer such as phosphate, which is generally included in the solution for adjusting its pH and which shows a relatively high degree of ionic strength when dissolved in water. It was also found that the ophthalmic solution exhibits a considerably higher germicidal or preservative effect than the conventional solution if concentrations of the sodium chloride and the phosphate in the solution are made zero or minimized and if at least one amino-acid-based component selected from the group consisting of selected amino acids, salts of the amino acids, and derivatives of the amino acids is used as a tonicity adjusting agent, in place of the sodium chloride.

The above-indicated first object of the present invention may be attained according to a first aspect of the invention, which provides an ophthalmic solution which comprises at least one germicidal/preservative component selected from the group consisting of biguamides and quaternary ammonium salts, further comprising: at least one amino-acid-based component selected from the group consisting of amino acids each having an isoelectric point of not smaller than 4 and a molecular weight of not smaller than 89, salts of the amino acids, and derivatives of the amino acids; and sodium chloride concentration of which in the ophthalmic solution is adjusted to be held in a range of 0–0.2 wt. % and phosphate concentration of which in the ophthalmic solution is adjusted to be held in a range of 0–0.5 wt. %.

In the present ophthalmic solution wherein the concentrations of the sodium chloride and the phosphate are made as low as possible, the biguamide germicide or the quaternary ammonium salt germicide exhibits its germicidal characteristics with significantly high efficiency. Accordingly, the present ophthalmic solution advantageously assures a sufficiently high degree of germicidal or preservative effect even if the concentration of the germicidal/preservative component included therein is minimized. Further, the use of the germicidal/preservative component in low concentrations effectively reduces the toxicity of the component, so that the present ophthalmic solution assures a high degree of safety to the living subject.

In the present ophthalmic solution wherein at least one amino-acid-based component selected from the group consisting of amino acids each having an isoelectric point of not smaller than 4 and a molecular weight of not smaller than 89, salts of the amino acids, and derivatives of the amino acids is used as the tonicity adjusting agent, in place of the sodium chloride conventionally used as the tonicity adjusting agent, the osmotic pressure of the ophthalmic solution can be adjusted without adversely influencing the germicidal activity of the germicidal/preservative component. Accordingly, it is not necessary to use the germicidal/preservative component in high concentrations in the present ophthalmic solution, so that the present ophthalmic solution is free from the conventionally experienced problem of irritation to the eye or the skin of the user due to the use of the germicidal/preservative component in relatively high concentrations.

Though the germicidal mechanism exhibited by the present ophthalmic solution is not clear, the inventors speculate as follows. The germicidal activity is exhibited when positively charged sites of the germicidal/preservative component included in the ophthalmic solution combine or couple with negatively charged sites located on the surfaces of microorganisms such as bacteria. Due to the electrolyte such as the sodium chloride or the buffer such as the phosphate buffer dissolved in the ophthalmic solution, positive ions and negative ions having relatively small sizes get in between the microorganisms and the germicidal component, reducing an electric attraction or binding force therebetween, whereby the germicidal activity of the germicidal component is inhibited. Further, the germicidal activity is inhibited due to the electrolyte which changes the structure of the germicidal component in the ophthalmic solution. The present ophthalmic solution is free from such inhibitory actions caused by the electrolyte and the buffer, for thereby assuring improved germicidal efficacy.

In one preferred form of the above-described first aspect of the invention, the isoelectric point of the at least one amino-acid-based component is not smaller than 5. According to this arrangement, the present ophthalmic solution exhibits further improved germicidal effect.

In another preferred form of the above-described first aspect of the invention, the at least one amino-acid-based component is neutral or basic. This arrangement assures an excellent germicidal effect.

Preferably, the at least one amino-acid-based component includes, in its one molecule, at least one acidic group which derives from carboxylic acid or sulfuric acid, and at least one basic group which derives from amino group or imino group. Preferably, a ratio of the at least one acidic group to the at least one basic group is held in a range of 1:1–1:4.

Preferably, the amino acids are γ-aminobutyric acid, alanine, cysteine, serine, taurine, threonine, valine, histidine, 4-hydroxyproline, phenylalanine, proline, ε-aminocaproic acid, lysine, and arginine.

The use of the lysine or arginine not only assures a high degree of germicidal effect, but also minimizes swelling of a contact lens when the present ophthalmic solution is used as a contact lens solution.

In still another preferred form of the above-described first aspect of the invention, the ophthalmic solution further includes glycerin. The inclusion of the glycerin in the ophthalmic solution particularly effectively prevents the irritation to the eye and skin of the user.

In yet another preferred form of the above-described first aspect of the invention, the at least one amino-acid-based component has an osmotic pressure of not lower than 50 mOsm/kg in 0.1 mol/L aqueous solution thereof. This arrangement advantageously prevents a need of using the at least one amino-acid-based component in an excessively large amount.

The present invention also provides a solution for a contact lens, especially for a soft contact lens, which is formed of the ophthalmic solution described above. In the contact lens solution or the soft contact lens solution according to the present invention, the concentration of the germicidal/preservative component included in the solution is made as low as possible while permitting the solution to exhibit an intended germicidal effect. Accordingly, the present contact lens solution or the soft contact lens solution assures a high degree of safety to the eye of the user.

As a result of an extensive study made by the inventors of the present invention to attain the above-indicated second and third objects of the invention relating to the contact lens solution (including a sterilizing solution, a preservative solution, etc.), it was found that if the concentration of the sodium chloride in the contact lens solution which includes the germicidal/preservative component such as the biguamide or the quaternary ammonium salt is made zero or minimized and if at least one predetermined acidic component such as glycolic acid, lactic acid, gluconic acid, aspartic acid, glutamic acid, or pyrophosphoric acid is used in place of the sodium chloride, the germicidal component (the preservative component) is effectively prevented from being adsorbed on or sticking to the contact lens, so that the contact lens solution exhibits a high degree of safety to the eye of the user without causing any trouble with the eye such as the inflammation of the eye or the staining of the cornea over the substantially entire surface with fluorescein described above.

It was also found that if the concentration of the sodium chloride in the contact lens solution which includes the germicidal/preservative component such as the biguamide or the quaternary ammonium salt is made zero or minimized and if at least one amino-acid-based component selected from the group consisting of selected amino acids, salts of the amino acids, and derivatives of the amino acids, and at least one predetermined acidic compound are used in combination, in place of the sodium chloride, the contact lens solution exhibits excellent compatibility with the contact lens without causing an undesirable change of the size of the contact lens, in addition to an excellent germicidal or preservative effect and a high degree of safety to the eye of the user.

The above-indicated second object of the present invention may be attained according to a second aspect of the invention, which provides a solution for a contact lens which comprises at least one germicidal/preservative component selected from the group consisting of biguamides and quaternary ammonium salts, further comprising: at least one acidic component selected from the group consisting of glycolic acid, lactic acid, gluconic acid, aspartic acid, glutamic acid, and pyrophosphoric acid; and sodium chloride concentration of which in the solution is adjusted to be held in a range of 0–0.2 wt. %.

Like the above-described ophthalmic solution according to the first aspect of the invention, the present contact lens solution wherein the concentration of the sodium chloride conventionally used as the tonicity adjusting agent is made as low as 0 to 0.2 wt. % permits the biguamide germicide or the quaternary ammonium salt germicide to effectively exhibit its germicidal effect. Further, the at least one acidic component selected from the group consisting of glycolic acid, lactic acid, gluconic acid, aspartic acid, glutamic acid, and pyrophosphoric acid is included in the contact lens solution in place of the sodium chloride conventionally used as the tonicity adjusting agent, whereby the osmotic pressure of the contact lens solution is adjusted to a desired level while preventing adsorption of the germicidal or preservative component included in the contact lens solution on the contact lens. Accordingly, the present contact lens solution assures a high degree of safety to the eye of the user without causing any trouble with the eye such as the inflammation of the eye or the staining of the cornea over the substantially entire surface with fluorescein described above.

In one preferred form of the above-described second aspect of the invention, the at least one acidic component has a concentration held in a range of 0.001–5 wt. %.

In another preferred form of the above-described second aspect of the invention, the contact lens solution further includes glycerin.

In still another preferred form of the above-described second aspect of the invention, the at least one germicidal/preservative component has a concentration held in a range of 0.000001–0.3 wt. %.

In yet another preferred form of the above-described second aspect of the invention, the contact lens solution has a pH in a range of 6–8.

The above-described third object of the present invention may be attained according to a third aspect of the invention, which provides a solution for a contact lens which comprises at least one germicidal/preservative component selected from the group consisting of biguamides and quaternary ammonium salts, further comprising: at least one amino-acid-based component selected from the group consisting of amino acids each having an isoelectric point of not smaller than 4 and a molecular weight of not smaller than 89, salts of the amino acids, and derivatives of the amino acids; at least one acidic compound which has at least one carboxyl group or at least one phosphoric acid group and which does not generate metal ions in an aqueous solution thereof and sodium chloride concentration of which in the solution is adjusted to be held in a range of 0–0.2 wt. %.

Like the contact lens solution according to the above-described second aspect of the invention, the present contact lens solution wherein the concentration of the sodium chloride conventionally included as the tonicity adjusting agent is made as low as 0 to 0.2 wt. % is free from deterioration of the germicidal effect to be exhibited by the biguamide germicide or the quaternary ammonium salt germicide. Accordingly, the germicidal effect can be effectively achieved even if the concentration of the germicidal component included in the contact lens solution is relatively low. Moreover, in place of the sodium chloride, the at least one amino-acid-based component selected from the group consisting of amino acids each having an isoelectric point of not smaller than 4 and a molecular weight of not smaller than 89, salts of the amino acids, and derivatives of the amino acids, is used in combination with the at least one acidic compound which has at least one carboxyl group or at least one phosphoric acid group and which does not generate metal ions in an aqueous solution thereof. Accordingly, the germicidal effect exhibited by the germicidal/preservative component is improved owing to the use of the at least one amino-acid-based component, so that the present contact lens solution is capable of exhibiting a high degree of germicidal effect. In addition, the at least one acidic compound effectively prevents adsorption of the germicidal component on the contact lens, so that the present contact lens solution assures a sufficiently high degree of safety to the eye of the user without causing any trouble with the eye such as the inflammation of the eye or the staining of the cornea over the substantially entire surface with the fluorescein described above. The combined use of the at least one amino-acid-based component and the at least one acidic compound is effective to prevent an undesirable change of the size of the contact lens due to swelling or shrinkage of the contact lens, whereby the present contact lens solution exhibits excellent compatibility with the contact lens.

As the acidic compound, at least one of glycolic acid, citric acid, lactic acid, gluconic acid, aspartic acid, glutamic acid, phosphoric acid, and pyrophosphoric acid is suitably used preferably in a concentration of 0.001–5 wt. %.

In one preferred form of the above-described third aspect of the present invention, the contact lens solution further includes glycerin. The inclusion of the glycerin in the contact lens solution is effective to prevent the user's eye from suffering from irritation.

In another preferred form of the above-described third aspect of the present invention, the at least one germicidal/preservative component has a concentration held in a range of 0.000001–0.3 wt. % (0.01 ppm–3000 ppm), while the at least one amino-acid-based component has a concentration preferably held in a range of 0.01–5 wt. %.

In still another preferred form of the above-described third aspect of the present invention, the at least one amino-acid-based component has an osmotic pressure of not lower than 50 mOsm/kg in 0.1 mol/L aqueous solution thereof. This arrangement is effective to prevent a need of using the amino-acid-based component in an excessively large amount.

In yet another preferred form of the above-described third aspect of the present invention, the contact lens solution has a pH in a range of 6–8. The contact lens solution whose Ph is kept in the range described above is effective to prevent or minimize various trouble such as eye irritation.

DETAILED DESCRIPTION OF THE PREFERRED EMBODIMENTS

There will be described in detail an ophthalmic solution produced according to a first embodiment of the present invention to attain the above-indicated first object of the invention. The ophthalmic solution according to the present embodiment is constituted principally by water, and includes: (1) at least one selected germicidal or preservative component (hereinafter referred to as "Component A"); and (2) at least one amino-acid-based component (hereinafter referred to as "Component B") selected from the group consisting of selected amino acids, salts of the amino acids, and derivatives of the amino acids, as a tonicity adjusting agent. In the present ophthalmic solution, the amounts of sodium chloride and phosphate which are included in the solution and which inhibit or deteriorate the germicidal effect of the Component A are made zero or minimized, for thereby permitting the ophthalmic solution to effectively exhibit its germicidal effect.

As the Component A to be included in the present ophthalmic solution, it is preferable to select from among known biguamide germicides and known quaternary ammonium salt germicides, which exhibit a high degree of compatibility with the contact lens, the eye, and the skin of the user, as well as a high degree of germicidal effect, and which do not cause undesirable trouble with the eye such as allergy. Any one of or any combinations of the biguamide germicides and the quaternary ammonium salt germicides can be suitably employed.

Examples of the biguamide germicide include polyhexamethylene biguamide (PHMB), and biguamide polymer which is represented by the following formula (I):

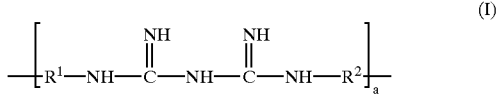
(I)

wherein, a represents an integer of not smaller than 1; and each of $R^1$ and $R^2$ independently represents a divalent group represented by $C_nH_mO_p$, wherein n=1–24, m=2–48, and p=0–11.

As the quaternary ammonium salt germicide, cationic surfactants are suitably used. The cationic surfactants include: alkyl ammonium salts such as tetraalkyl ammonium salts which include alkyltrimethylammonium chloride, and trialkylbenzyl ammonium salts which include octadecyl dimethylbenzyl ammonium chloride; quaternary salts of alkylhydroxy alkylimidazoline whose typical example is hydroxyethyl alkylimidazoline chloride; alkylisoquinolinium salts whose typical example is alkylisoquinolinium bromide; alkylpyridinium salts; and amideamines. Further, as the quaternary ammonium salt germicide, there may be used quaternary ammonium polymers represented by the following formulas (II)–(IV), condensation products of diamines and dihalogen compounds as disclosed in Japanese Patent No. 2550036, polycationic surfactants disclosed in JP-A-4-231054, JP-A-8-512145, and JP-A-11-249087, and benzalkonium halide.

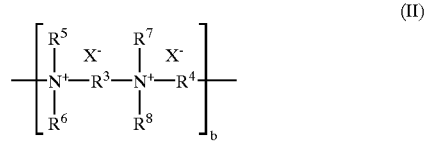
(II)

wherein b represents an integer of not smaller than 1; $X^-$ represents monovalent anion such as $Cl^-$; each of $R^3$ and $R^4$ independently represents a divalent group represented by $C_nH_mO_p$, wherein n=1–24, m=2–48, and p=0–11; and each of $R^5$, $R^6$, $R^7$, and $R^8$ independently represents a monovalent group represented by $C_qH_rO_s$, wherein q=1–4, r=2–9, and s=0–1.

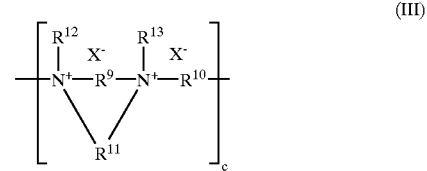
(III)

wherein, c represents an integer of not smaller than 1; $X^-$ represents monovalent anion such as $Cl^-$; each of $R^9$ and $R^{10}$ independently represents a divalent group represented by $C_nH_mO_p$, wherein n=1–24, m=2–48, and p=0–11; $R^{11}$ represents a divalent group represented by $C_tH_uO_v$, wherein t=1–4, u=2–9, and v=0–1; and each of $R^{12}$ and $R^{13}$ independently represents a monovalent group represented by $C_qH_rO_s$, wherein q=1–4, r=2–9, and s=0–1.

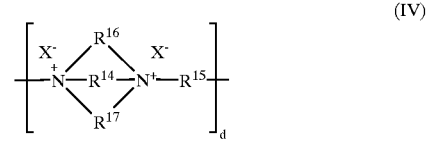
(IV)

wherein, d represents an integer of not smaller than 1; $X^-$ represents monovalent anion such as $Cl^-$; each of $R^{14}$ and $R^{15}$ independently represents a divalent group represented by $C_nH_mO_p$, wherein n=1–24, m=2–48, and P=0–11; and each of $R^{16}$ and $R^{17}$ independently represents $C_tH_uO_v$, wherein t=1–4, u=2–9, and v=0–1.

The Component A is used generally in an amount of about 0.000001–0.3 wt. % (w/w %), preferably in an amount of about 0.00001–0.1 wt. % (w/w %) for assuring a particularly effective germicidal or preservative effect. If the amount of the Component A to be used is excessively small, the ophthalmic solution does not exhibit a sufficiently high degree of germicidal or preservative effect. On the other hand, the amount of the Component A exceeding the upper limit of 0.3 wt. % results in an increase of the toxicity, giving adverse influences on the eye and the skin of the user. Further, the Component A tends to be adsorbed on the surface of the contact lens. Thus, the use of the excessively large amount of the Component A may give rise to a problem of insufficient safety.

For permitting the ophthalmic solution which includes the Component A described above to exhibit an effective germicidal or preservative efficacy, it is preferable that the ophthalmic solution does not include a strong electrolyte such as sodium chloride or potassium chloride generally used as a tonicity adjusting agent since such a strong electrolyte inhibits the germicidal activity of the Component A. Even in a case where the sodium chloride, etc. is included in the ophthalmic solution, the concentration of the sodium chloride should be adjusted to 0.2 wt. % (w/w %) or lower.

The concentration of the sodium chloride in the ophthalmic solution held in a range of 0–0.2 wt. %, however, undesirably makes the osmotic pressure of the ophthalmic solution too low. In view of this, the ophthalmic solution according to the present embodiment includes, as the tonicity agent, at least one Component B (amino-acid-based component) having an isoelectric point of not smaller than 4, preferably not smaller than 5, and a molecular weight of not smaller than 89. If the isoelectric point of the Component B is less than 4, the germicidal activity of the Component A is inhibited, so that the ophthalmic solution does not exhibit the intended germicidal effect. If the molecular weight of the Component B is less than 89, the molecular size of the Component B is undesirably small, so that the Component B tends to be adsorbed on the surface of the contact lens and stored in the contact lens when the ophthalmic solution is used as a contact lens solution (contact lens sterilizing solution, etc.).

The Component B whose isoelectric point is not smaller than 4 is generally neutral or basic. In the present invention, the neutral or basic Component B is preferably employed. In particular, it is preferable to employ the Component B which includes, in its one molecule, at least one acidic group which derives from carboxylic acid or sulfuric acid, and at least one basic group which derives from amino group or imino group. Preferably, a ratio of the at least one acidic group to the at least one basic group is held in a range of 1:1–1:4. The use of the Component B described above permits the ophthalmic solution to exhibit a further improved germicidal effect.

Any suitable Component B may be employed as long as it satisfies the above-described conditions and assures a high level of safety. For instance, examples of the neutral amino acid include: alkyl-group-containing amino acids such as alanine, isoleucine, valine, leucine, and proline; hydroxyl-group-containing amino acids such as serine, threonine, and 4-hydroxyproline; thio-group-containing amino acids such as cysteine and methionine; and asparagine. Examples of the basic amino acid include lysine, histidine, and arginine. In addition, the following neutral and basic amino acids, and the derivatives thereof may be used, e.g., $\alpha$-aminobutyric acid, $\gamma$-aminobutyric acid, $\beta$-alanine, alloisoleucine, allothreonine, ethionine, ornithine, glutamine, creatine, sarcosine, cystathionine, taurine, norvaline, norleucine, $\delta$-hydroxylysine, phenylalanine, homoserine, aminocaproic acid, and theanine. Examples of the salts of the amino acids described above include: hydrochlorides such as ornithine hydrochloride, cysteine hydrochloride, histidine hydrochloride, lysine hydrochloride, and arginine hydrochloride; organic salts such as lysine acetate; and composite salts formed of at least two kinds of amino acids such as glutamine-lysine composite salt. Any one of or any combination of the amino acids, the salts of the amino acids, and the derivatives of the amino acids described above may be suitably employed as the Component B. The Component B described above is effective to improve the germicidal effect exhibited by the Component A. The germicidal effect of the Component A can be kept at high levels by the neutral amino acid, the basic amino acid, and the acidic amino acid, in the order of description. The basic amino acid is superior to the neutral and acidic amino acids in compatibility with the contact lens, while permitting the Component A to exhibit a high degree of germicidal effect. In particular, the lysine and the arginine advantageously exhibit such characteristics.

The above-described Component B is used in place of the strong electrolyte inorganic salt such as the sodium chloride or the potassium chloride generally used for adjusting the osmotic pressure of the conventional ophthalmic solution. In the present ophthalmic solution, the Component B is used generally in an amount of 0.5–6.0 wt. % (w/w %), preferably in an amount of 1.0–4.5 wt. % (w/w %), so that the osmotic pressure of the ophthalmic solution is adjusted to a level substantially equal to the physiological osmotic pressure, i.e., about 250–400 mOsm/kg, for thereby avoiding irritation to the eye and the skin of the user. If the amount of the Component B is excessively small, the osmotic pressure of the ophthalmic solution may be too low. On the other hand, the use of the Component B in an amount exceeding the upper limit may undesirably cause a significant increase of the osmotic pressure of the ophthalmic solution.

In order to avoid the use of the excessively large amount of the Component B, it is preferable to employ the Component B which has an osmotic pressure of generally not lower than 50 mOsm/kg, preferably not lower than 80 mOsm/kg, in 0.1 mol/L aqueous solution thereof. If the osmotic pressure of the Component B is excessively low, the amount of the Component B which is required to establish the intended osmotic pressure of the ophthalmic solution is inevitably increased. In this case, the germicidal activity of the Component A tends to be adversely influenced, resulting in a decrease of the germicidal effect. Further, the solubility of the Component B may deteriorate, resulting in precipitation of the Component B. Moreover, the use of the excessively large amount of the Component B inevitably pushes up the cost of production of the ophthalmic solution. In addition, the viscosity of the ophthalmic solution may be undesirably increased due to the use of the excessively large amount of the Component B, resulting in a change of the quality of the ophthalmic solution such as deterioration of a feel of the solution as felt by the user.

In the present ophthalmic solution wherein at least one amino-acid-based component (Component B) selected from the group consisting of the selected amino acids, the salts of the amino acids, and the derivatives of the amino acids is used as the tonicity adjusting agent, in place of the strong electrolyte such as the sodium chloride which has a high degree of ionic strength, the biguamide germicide or the quaternary ammonium salt germicide exhibits its germicidal effect with significantly high efficiency.

The present ophthalmic solution may further include, as needed, glycerin (hereinafter referred to as "Component D") as a tonicity adjusting agent, in addition to the Component B. The addition of the glycerin is effective to protect the eye and the skin of the user from suffering from irritation.

The present ophthalmic solution may further include, as needed, various known additives such as a pH adjusting agent, a buffer, a surfactant, a chelating agent, a thickener, etc, which additives are conventionally used in liquid agents such as contact lens solutions including a collyrium and a contact lens sterilizing solution, and cosmetics.

Where the present ophthalmic solution is used as the contact lens solutions such as the collyrium and the contact lens sterilizing solution, and the cosmetics, which are applied to the eye and the skin of the living subject, the pH of the ophthalmic solution is preferably adjusted to be held in a range of 4.0–9.0, more preferably in a range of 6.0–8.0 when used as the contact lens solutions, in particular in the vicinity of 7.0, so as to avoid irritation or troubles to the eye and the skin of the user. To this end, a pH adjusting agent such as sodium hydroxide, potassium hydroxide, or hydrochloric acid may be added to the ophthalmic solution. Like the sodium chloride, the pH adjusting agent described above is also a strong electrolyte. Accordingly, it is necessary to minimize the amount of the pH adjusting agent to be included in the ophthalmic solution. Where the ophthalmic solution includes ions which constitute the strong electrolyte inorganic salt such as the sodium chloride due to the addition of the strong alkali or the strong acid to the ophthalmic solution, it is needless to say that the concentration of the sodium chloride in the ophthalmic solution, including the sodium chloride formed by the addition of the strong alkali or acid, must be adjusted to a level of not higher than 0.2 wt. %.

In order to keep the pH of the ophthalmic solution at the level described above for assuring safety to the eye and the skin of the user, the present ophthalmic solution may include a buffer known in the art. For assuring a high degree of safety to the eye and the skin of the user and minimizing the influence on the contact lens, the buffer is preferably selected, for instance, from among a citrate buffer, a phosphate buffer, a borate buffer, a carbonate buffer, a tris (hydroxymethyl)aminomethane (TRIS) buffer, and a Good-Buffer such as Bis-Tris. The buffer is added to the present ophthalmic solution generally in an amount of about 0.01–2 wt. % (w/w %). Where the buffer which shows a relatively high degree of ionic strength when dissolved in water, e.g., the phosphate buffer and the citrate buffer, is used, the germicidal activity of the Component A may be adversely influenced by such a buffer. In this case, the amount of the buffer needs to be made zero, or made as small as possible.

Described more specifically, if the pH of the ophthalmic solution is adjusted by the phosphate buffer or the citrate buffer, the amount of the buffer to be added is determined such that the concentration of the buffer is held in a range of 0–0.5 wt. %. If the buffer is used in amounts which do not fall within the range described above, the germicidal activity of the Component A is adversely influenced by the buffer, even if the amount of the strong electrolyte such as the sodium chloride in the ophthalmic solution is minimized. In this case, the ophthalmic solution does not exhibit the intended germicidal effect.

The present ophthalmic solution may further include a surfactant as a cleaning agent, so that the ophthalmic solution exhibits an effect of removing deposits such as eye lipid from the contact lens, in other words, the ophthalmic solution exhibits a cleaning effect. Any suitable surfactants known in the art may be used as long as they assure a high degree of safety to the living subject without giving an adverse influence on the material of the contact lens. The surfactant is added to the ophthalmic solution in suitable concentrations so as not to adversely influence the effect of the present invention.

Examples of the surfactant include polyglycerin fatty acid ester, polyoxyethylene alkyl ether, polyoxyethylene-polyoxypropylene block copolymer, polyoxyethylene-polyoxypropylene ethylene diamine, polyoxyethylene sorbitan fatty acid ester, condensation product of polyoxyethylene alkylphenyl ether and formaldehyde, polyoxyethylene hardened castor oil, polyoxyethylene alkylphenyl ether, polyoxyethylene glycerin fatty acid ester, polyoxyethylene sorbitol fatty acid ester, polyoxyethylene castor oil, polyoxyethylene sterol, polyoxyethylene hydrogenated sterol, polyoxyethylene fatty acid ester, polyoxyethylene-polyoxypropylene alkyl ether, polyoxyethylene lanolin alcohol, polyoxyethylene alkyl amine, polyoxyethylene alkyl amide, polyoxyethylene alkyl ether phosphoric acid, and polysorbate.

The surfactant is added to the ophthalmic solution generally in an amount of about 0.001–5 wt. % (w/w %), preferably in an amount of about 0.005–2 wt. % (w/w %), and more preferably in an amount of about 0.01–1 wt. % (w/w %). The amount of the surfactant smaller than the lower limit results in an insufficient cleaning effect. The cleaning effect does not significantly improve even if the surfactant is used in an amount which exceeds the upper limit. On the contrary, the amount of the surfactant exceeding the upper limit may even cause irritation to the eye.

The present ophthalmic solution may further include a thickener, as needed. Examples of the thickener include: gums such as heteropolysaccharide: synthetic organic high-molecular compounds such as polyvinyl alcohol, poly-N-vinylpyrrolidone, polyethylene glycol, polypropylene glycol, and polyacrylamide; cellulose derivatives; and starch derivatives.

Any other known additives such as a chelating agent may be included, as needed, in the present ophthalmic solution, as long as the additives are safe to the living subject without adversely influencing the material of the contact lens.

Where the present ophthalmic solution is used as the contact lens solution, a metal chelating agent is preferably included therein for preventing metal ions such as calcium in the tear fluid from adhering to the contact lens, especially, the soft contact lens. Examples of the metal chelating agent include: ethylenediamine tetraacetic acid (EDTA) and salts thereof such as disodium salts of ethylenediamine tetraacetic acid (EDTA•2Na) and trisodium salts of ethylenediamine tetraacetic acid (EDTA•3Na). The metal chelating agent is included generally in an amount of 0.01–1.0 wt. % (w/w %), so as not to adversely influence the effect of the present invention.

The present ophthalmic solution which includes the Component A and the Component B described above is prepared according to any known manner as usually employed for preparing ordinary aqueous solutions, without requiring any special procedure. For instance, the present ophthalmic solution is easily prepared by dissolving each component in an aqueous medium such as purified water or distilled water.

The present ophthalmic solution prepared as described above is suitably used as the solution for the contact lens, especially for the soft contact lens, the collyrium, and the preservative added to the cosmetics.

Where the present ophthalmic solution prepared as described above is used as the contact lens solution, the contact lens is treated in the following manner. Initially, the contact lens which has been removed from the eye is immersed, for a predetermined time period, in the present ophthalmic solution in the form of the contact lens solution which is accommodated in a suitable container, so that the contact lens is disinfected. The contact lens which has been immersed in the solution is cleaned before wearing the contact lens. The contact lens may be simply rinsed with a physiological saline without being cleaned. Alternatively, the contact lens which has been immersed in the present solution may be directly worn on the eye without rinsing since the present solution is safe to the eye. The contact lens may be cleaned before it is immersed in the present solution for disinfection.

The contact lens solution according to the present invention is applied to any known kinds of contact lenses such as non-water-absorbable or non-water-content, low-water-content, and high-water-content soft contact lenses, and hard contact lenses, irrespective of the materials of those contact lenses. The present contact lens solution is advantageously applied to the soft contact lenses which particularly require disinfection.

There will next be described a contact lens solution produced according to a second embodiment of the present invention to attain the above-indicated second object of the invention. The contact lens solution according to the second embodiment is constituted principally by water, and includes: (1) at least one selected germicidal or preservative component, i.e., the Component A described above with respect to the first embodiment; and (2) at least one selected acidic component (hereinafter referred to as "Component C"). In the present contact lens solution, the amount of the sodium chloride which inhibits or deteriorates the germicidal activity of the Component A is made zero or minimized. In the present contact lens solution described above, the adsorption of the Component A on the contact lens is effectively prevented while avoiding deterioration of the germicidal effect exhibited by the Component A, whereby the present contact lens solution assures a sufficiently high degree of safety.

As the Component A to be included in the present contact lens solution, it is preferable to select from among known biguamide germicides and known quaternary ammonium salt germicides, which exhibit a high degree of compatibility with the contact lens and the eye of the user, as well as a high degree of germicidal effect, and which do not cause undesirable trouble with the eye such as allergy. Any one of or any combination of the biguamide germicides and the quaternary ammonium salt germicides described above with respect to the ophthalmic solution according to the first embodiment are suitably employed.

The Component A is used generally in an amount of about 0.000001–0.3 wt. % (w/w %), preferably in an amount of about 0.00001–0.1 wt. % (w/w %). If the amount of the Component A to be used is excessively small, the germicidal or preservative effect is insufficient. On the other hand, the amount of the Component A exceeding the upper limit increases adsorption of the Component A on the surface of the contact lens. In this case, the eye of the user may be adversely influenced by the Component A, giving rise to a problem of insufficient safety.

For permitting the present contact lens solution which includes the Component A described above to exhibit an effective germicidal or preservative efficacy, it is preferable that the contact lens solution does not include the strong electrolyte such as the sodium chloride or the potassium chloride generally used as the tonicity adjusting agent since such a strong electrolyte inhibits the germicidal activity of the Component A. Even in a case where the sodium chloride, etc. is included in the contact lens solution, the concentration of the sodium chloride should be adjusted to 0.2 wt. % (w/w %) or lower. The concentration of the sodium chloride in the contact lens solution held in a range of 0–0.2 wt. %, however, undesirably makes the osmotic pressure of the solution too low. In view of this, the contact lens solution according to the present embodiment includes, as the tonicity agent, the acidic component (the Component C).

As the Component C, at least one of glycolic acid, lactic acid, gluconic acid, aspartic acid, glutamic acid, and pyrophosphoric acid is suitably employed. The Component C is effective to prevent the Component A from adhering to the contact lens. While the mechanism for this is not clear, the inventors of the present invention speculate that the adsorption of the Component A having positive charges is prevented by the Component C having negative charges.

The Component C does not cause a significant change of the size of the contact lens immersed in the present contact lens solution. Accordingly, the present contact lens solution exhibits suitable compatibility with the contact lens.

In the present contact lens solution, the Component C is used generally in an amount of 0.001–5.0 wt. % (w/w %), preferably in an amount of 0.01–4.0 wt. % (w/w %), so that the osmotic pressure of the solution is adjusted to a level substantially equal to the physiological osmotic pressure, i.e., 250–400 mOsm/kg, for thereby avoiding irritation to the eye of the user. If the amount of the Component C is excessively small, the effect to be provided by the Component C is insufficient. On the other hand, the use of the Component C in an amount exceeding the upper limit may undesirably cause a significant increase of the osmotic pressure of the contact lens solution.

In the present contact lens solution, in place of the strong electrolyte such as the sodium chloride which shows a high ionic strength, the at least one Component C selected from the group consisting of glycolic acid, lactic acid, gluconic acid, aspartic acid, glutamic acid, and pyrophosphoric acid is used as the tonicity adjusting agent. This arrangement is effective to prevent deterioration of the germicidal effect of the Component A and adsorption of the Component A on the contact lens. Thus, the present contact lens solution assures a high degree of safety to the eye of the user without causing any trouble with the eye such as the inflammation of the eye and the staining of the cornea over the substantially entire surface with the fluorescein.

Like the ophthalmic solution according to the above-described first embodiment, the present contact lens solution may further include, as needed, the glycerin (Component D) as the tonicity adjusting agent. The addition of the glycerin is effective to protect the eye from suffering from irritation.

Like the ophthalmic solution according to the above-described first embodiment, the present contact lens solution has a pH of generally in a range of 6.0–8.0, preferably in the vicinity of 7.0, so as to avoid irritation or trouble to the eye. To this end, a pH adjusting agent such as sodium hydroxide, potassium hydroxide, or hydrochloric acid, or a buffer may be added to the contact lens solution. Like the sodium chloride, the pH adjusting agent described above is also a strong electrolyte. Accordingly, it is necessary to minimize the amount of the pH adjusting agent to be included in the contact lens solution. Where the contact lens solution includes ions which constitute the strong electrolyte inorganic salt such as the sodium chloride due to the addition of the strong alkali or the strong acid to the solution, it is needless to say that the concentration of the sodium chloride in the solution, including the sodium chloride formed by the addition of the strong alkali or acid, must be adjusted to a level of not higher than 0.2 wt. %. Any known buffers are suitably employed in amounts that do not adversely influence the effect of the present invention.

Any other known additives used in conventional contact lens solutions may be added to the present contact lens solution, as needed. For instance, the surfactant, the chelating agent, and the thickener described above with respect to the ophthalmic solution according to the first embodiment may be added to the present contact lens solution in amounts similar to those in the ophthalmic solution.

Like the ophthalmic solution according to the first embodiment, the present contact lens solution is prepared according to any known manner as usually employed for preparing ordinary aqueous solutions, without requiring any special procedure. For instance, the present contact lens solution is easily prepared by dissolving each component in an aqueous medium such as purified water or distilled water. The thus prepared contact lens solution according to the present embodiment is advantageously used as a contact lens sterilizing solution, a contact lens sterilizing and cleaning solution, a contact lens sterilizing and storing solution, a contact lens sterilizing, cleaning and storing solution, or a contact lens cleaning and/or storing solution. The present contact lens solution is applied to any known kinds of contact lenses such as non-water-absorbable or non-water-content, low-water-content, and high-water-content soft contact lenses, and hard contact lenses.

Since the present contact lens solution assures a high degree of safety to the eye, the contact lens solution is used as the collyrium or eye drops.

There will next be described a contact lens solution produced according to a third embodiment of the present invention to attain the above-indicated third object of the invention. The contact lens solution according to this embodiment assures excellent compatibility with the eye without causing a change of the contact lens due to swelling or shrinkage, in addition to the advantages described above with respect to the ophthalmic solution according to the first embodiment and the contact lens solution according to the second embodiment.

Described more specifically, the contact lens solution according to the present embodiment is constituted principally by water, and includes: (1) at least one selected germicidal or preservative component, i.e., the Component A described above with respect to the ophthalmic solution according to the first embodiment and the contact lens solution according to the second embodiment; (2) at least one amino-acid-based component selected from the group consisting of selected amino acids, salts of the amino acids, and derivatives of the amino acids, i.e., the Component B described above with respect to the ophthalmic solution according to the first embodiment; and (3) at least one selected acidic component (hereinafter referred to as "Component C'"). In the present contact lens solution, the amount of the sodium chloride which inhibits or deteriorates the germicidal effect of the Component A is made zero or minimized. In the present contact lens solution described above, the germicidal effect is improved owing to the Component B even if the concentration of the Component A is relatively low, and the adsorption of the Component A on the contact lens is advantageously prevented owing to the Component C'. Moreover, the combined use of the Component B and the Component C' effectively prevents an undesirable change of the size of the contact lens.

As the Component A to be included in the present contact lens solution, it is preferable to select from among known biguamide germicides and known quaternary ammonium salt germicides, which exhibit a high degree of compatibility with the contact lens and the eye of the user, as well as a high degree of germicidal effect, and which do not cause undesirable trouble with the eye such as allergy. Any one of or any combination of the biguamide germicides and the quaternary ammonium salt germicides described above with respect to the ophthalmic solution according to the first embodiment are suitably employed.

The Component A is used generally in an amount of about 0.000001–0.3 wt. % (w/w %), preferably in an amount of about 0.00001–0.1 wt. % (w/w %).

As described above with respect to the ophthalmic solution according to the first embodiment, for permitting the present contact lens solution which includes the Component A described above to exhibit an effective germicidal or preservative efficacy, it is preferable that the contact lens solution does not include the strong electrolyte such as the sodium chloride or the potassium chloride generally used as the tonicity adjusting agent since such a strong electrolyte inhibits the germicidal activity of the Component A. Even in a case where the sodium chloride, etc. is included in the contact lens solution, the concentration of the sodium chloride in the solution should be adjusted to 0.2 wt. % (w/w %) or lower.

The concentration of the sodium chloride in the contact lens solution held in a range of 0–0.2 wt. %, however, undesirably makes the osmotic pressure of the solution too low. In view of this, in the contact lens solution according to the present embodiment, the at least one amino-acid-based component (Component B) selected from the group consisting of the selected amino acids, salts of the amino acids, and derivatives of the amino acids, and the at least one selected acidic compound (Component C') are used in combination as the tonicity adjusting agent, in place of the sodium chloride.

For the same reasons described above with respect to the ophthalmic solution according to the first embodiment, the Component B included in the contact lens solution according to the present embodiment preferably has an isoelectric point of not smaller than 4, more preferably not smaller than 5, and a molecular weight of not smaller than 89. Preferably, the Component B to be used is neutral or basic. In particular, it is preferable to employ the Component B which includes, in its one molecule, at least one acidic group which derives from carboxylic acid or sulfuric acid, and at least one basic group which derives from amino group or imino group. Preferably, a ratio of the at least one acidic group to the at least one basic group is held in a range of 1:1–1:4.

As described above with respect to the ophthalmic solution according to the first embodiment, it is preferable to employ the Component B which has an osmotic pressure of generally not lower than 50 mOsm/kg, preferably not lower than 80 mOsm/kg, in 0.1 mol/L aqueous solution thereof, in order to avoid a need of using an excessively large amount of the Component B. If the osmotic pressure of the Component B is excessively low, the amount of the Component B which is required to establish the intended osmotic pressure of the contact lens solution is inevitably increased. In this case, the germicidal activity of the Component A tends to be adversely influenced, resulting in a decrease of the germicidal effect. Further, the solubility of the Component B may deteriorate, resulting in precipitation of the Component B. Moreover, the use of the excessively large amount of the Component B inevitably pushes up the cost of production of the contact lens solution. In addition, the viscosity of the contact lens solution may be undesirably increased due to the use of the excessively large amount of the Component B, resulting in a change of the quality of the contact lens solution such as deterioration of a feel of the contact lens solution as felt by the user.

As the Component C' to be used in combination with the Component B, it is preferable to employ at least one acidic compound which has at least one carboxyl group or at least one phosphoric acid group and which does not generate metal ions. In other words, the at least one acidic compound is not metal salts such as sodium salts or potassium salts which generate metal ions such as sodium ions or potassium ions in an aqueous solution thereof.

Described more specifically, as the Component C', the acidic component (Component C) included in the contact lens solution according to the above-described second embodiment can be employed. Examples of the Component C' include glycolic acid, lactic acid, gluconic acid, aspartic acid, glutamic acid, pyrophosphoric acid, citric acid, phosphoric acid, nicotinic acid, benzoic acid, succinic acid, tartaric acid, malonic acid, and maleic acid. It is particularly preferable to employ, as the Component C', the glycolic acid, lactic acid, gluconic acid, aspartic acid, glutamic acid, pyrophosphoric acid, citric acid, and phosphoric acid.

At least one of the acidic compounds described above is suitably employed as the Component C'. Owing to the presence of the Component C' in the present contact lens solution, the adsorption of the Component A on the contact lens can be effectively prevented, so that the present contact lens solution assures a sufficiently high degree of safety to the eye of the user without causing any trouble with the eye such as the inflammation of the eye and the staining of the cornea over the substantially entire surface with the fluorescein.

Further, the combined use of the Component B and the Component C' more effectively prevents a change of the size of the contact lens due to swelling and shrinkage, and assures a higher degree of compatibility with the contact lens, than an arrangement wherein the Component B and the Component C' are not used in combination.

The reason why the present contact lens solution assures such excellent compatibility with the contact lens is speculated as follows. Where the contact lens is immersed in a solution which contains the Component B without containing the Component C', the contact lens immersed in the solution tends to be swollen, in other words, the size of the contact lens tends to be increased. Where the contact lens is immersed in a solution which contains the Component C' without containing the Component B, the contact lens immersed in the solution tends to be shrunk, in other words, the size of the contact lens tends to be decreased. Accordingly, the Component B which causes the swelling of the contact lens and the Component C' which causes the shrinkage of the contact lens are used in combination to prevent a change of the size of the contact lens, with a mutual counteraction between the swelling and shrinkage behaviors.

For advantageously obtaining various effects described above, the Component B is included in the contact lens solution generally in an amount of 0.01–5 wt. % (w/w %), preferably in an amount of 0.5–4.0 wt. % (w/w %), while the Component C' is included generally in an amount of 0.001–5.0 wt. % (w/w %), preferably in an amount of 0.01–2.0 wt. % (w/w %). Since the Component B and the Component C' function as the tonicity adjusting agent, in place of the sodium chloride, the amounts of the Component B and the Component C' to be added are determined such that the contact lens solution has an osmotic pressure substantially equal to the physiological osmotic pressure, i.e., in a range of 250–400 mOsm/kg.

In the contact lens solution according to the present embodiment wherein at least one Component B and at least one Component C' are used in combination, in place of the strong electrolyte such as the sodium chloride which has a high degree of ionic strength, the Component A (the biguamide germicide or the quaternary ammonium salt germicide) exhibits its germicidal effect with significantly high efficiency, and the adsorption of the Component A on the contact lens is effectively prevented. Therefore, the present contact lens solution assures improved safety to the eye of the user and excellent compatibility with the contact lens without suffering from a change of the size of the contact lens.

Like the ophthalmic solution according to the first embodiment described above and the contact lens solution according to the second embodiment described above, the contact lens solution according to the present embodiment may further contain, as needed, the glycerin (component D) as the tonicity adjusting agent. The inclusion of the glycerin in the contact lens solution minimizes the eye irritation.

Like the ophthalmic solution according to the first embodiment and the contact lens solution according to the second embodiment, the present contact lens solution has a pH of generally in a range of 6.0–8.0, preferably in the vicinity of 7.0, so as to avoid irritation or trouble to the eye. To this end, a pH adjusting agent such as sodium hydroxide, potassium hydroxide, hydrochloric acid, or a buffer may be added to the contact lens solution. Like the sodium chloride, the pH adjusting agent described above is also a strong electrolyte. Accordingly, it is necessary to minimize the amount of the pH adjusting agent to be included in the contact lens solution. Where the contact lens solution includes ions which constitute the strong electrolyte inorganic salt such as the sodium chloride due to the addition of the strong alkali or the strong acid to the solution, it is needless to say that the concentration of the sodium chloride in the solution, including the sodium chloride formed by the addition of the strong alkali or the strong acid, must be adjusted to a level not higher than 0.2 wt. %. Any known buffers are suitably employed in amounts that do not adversely influence the effect of the present invention.

Any known other additives used in conventional contact lens solutions may be added to the present contact lens solution, as needed. For instance, the surfactant, the chelating agent, and the thickener described above with respect to the ophthalmic solution according to the first embodiment may be added to the present contact lens solution in amounts similar to those in the ophthalmic solution.

Like the ophthalmic solution according to the first embodiment and the contact lens solution according to the second embodiment, the present contact lens solution is prepared according to any known manner as usually employed for preparing ordinary aqueous solutions, without requiring any special procedure. For instance, the present contact lens solution is easily prepared by dissolving each component in an aqueous medium such as purified water or distilled water. The thus prepared contact lens solution according to the present embodiment is advantageously used as a contact lens sterilizing solution, a contact lens sterilizing and cleaning solution, a contact lens sterilizing and storing solution, a contact lens sterilizing, cleaning and storing solution, or a contact lens cleaning and/or storing solution.

The present contact lens solution is applied to any known kinds of contact lenses such as non-water-absorbable or non-water-content, low-water-content, and high-water-content soft contact lenses, and hard contact lenses. The contact lens solution according to the present embodiment is advantageously applied to the soft contact lens which tends to suffer from a change of its size since the present contact lens solution exhibits excellent compatibility with the contact lens.

Since the present contact lens solution assures a high degree of safety to the eye, the contact lens solution is used as the collyrium or eye drops.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

<Example 1>

Initially, various ophthalmic solution specimens Nos. 1–14 were prepared by adding, to a predetermined amount of distilled water, a germicidal component (Component A), at least one amino-acid-based component (Component B) selected from the group consisting of selected amino acids, salts of the amino acids, and derivatives of the amino acids, and a chelating agent, so as to have respective different compositions as indicated in the following TABLE 1. Each of the solution specimens has an osmotic pressure of about 290 mOsm/kg and a pH of about 7.3 by adding, as needed, suitable amounts of hydrochloric acid or sodium hydroxide as a pH adjusting agent. As the Component A, polyhexamethylene biguamide (PHMB) was used. As the Component B (tonicity adjusting agent), different kinds of the amino-acid-based components having different isoelectric points as indicated in the following TABLE 2 were used. TABLE 2 also shows the pH and the osmotic pressure of the Component B, as measured in its 0.1 mol/L aqueous solution, together with the molecular weight. As the chelating agent, disodium salt of ethylenediamine tetraacetic acid (EDTA·2Na) was used.

TABLE 1

| Specimens | Contents (w/w %) | | |
|---|---|---|---|
| | PHMB | Component B | EDTA · 2Na |
| 1 | 0.0001 | 2.4 | 0.05 |
| 2 | 0.0001 | 2.8 | 0.05 |
| 3 | 0.0001 | 2.7 | 0.05 |
| 4 | 0.0001 | 2.7 | 0.05 |
| 5 | 0.0001 | 2.9 | 0.05 |
| 6 | 0.0001 | 3.3 | 0.05 |
| 7 | 0.0001 | 3.2 | 0.05 |
| 8 | 0.0001 | 2.7 | 0.05 |
| 9 | 0.0001 | 3.4 | 0.05 |
| 10 | 0.0001 | 4.2 | 0.05 |
| 11 | 0.0001 | 3.5 | 0.05 |
| 12 | 0.0001 | 2.5 | 0.05 |
| 13 | 0.0001 | 1.8 | 0.05 |
| 14 | 0.0001 | 3.1 | 0.05 |

(0.0001 w/w % = 1 ppm)

TABLE 2

| Specimens | Component B | Isoelectric point | Molecular weight | Characteristics in 0.1 mol/L aqueous solution | |
|---|---|---|---|---|---|
| | | | | pH | Osmotic pressure [mOsm/kg] |
| 1 | DL-alanine | 6.00 | 89.09 | 6.05 | 104 |
| 2 | L-valine | 5.96 | 117.2 | 7.83 | 103 |
| 3 | L-proline | 6.30 | 115.1 | 5.90 | 104 |
| 4 | L-serine | 5.68 | 105.1 | 6.12 | 105 |
| 5 | L-threonine | 6.16 | 119.1 | 5.88 | 102 |
| 6 | L-oxyproline | 5.83 | 131.1 | 5.87 | 105 |
| 7 | L-cysteine | 5.07 | 121.2 | 5.86 | 102 |
| 8 | γ-aminobutyric acid | 7.30 | 103.1 | 5.96 | 107 |
| 9 | taurine | 4.50 | 125.15 | 5.19 | 106 |
| 10 | L-phenylalanine | 5.48 | 165.2 | 6.14 | 105 |
| 11 | ε-aminocaproic acid | 7.60 | 131.18 | 7.54 | 106 |
| 12 | lysine hydrochloride | 9.74 | 182.7 | 5.91 | 105 |
| 13 | L-histidine hydrochloride | 7.59 | 191.7 | 5.80 | 105 |
| 14 | arginine hydrochloride | 10.76 | 210.7 | 5.62 | 181 |

9.9 mL of the solution specimens prepared as described above were put into respective test tubes. To each of the test tubes, there was added 0.1 mL of fungi liquid which contained *Candida albicans* IFO 1594 in an amount of $10^8$–$10^9$ cfu/mL. The mixture of the solution and the fungi liquid was stirred, so as to provide a fungi suspension which includes the fungi in an amount of $10^6$–$10^7$ cfu/mL. The thus obtained fungi suspensions according to the solution specimens Nos. 1–13 were kept at 23° C. for one hour. The fungi suspension according to the solution specimen No. 14 was kept at 23° C. for four hours. Thereafter, 1 mL of the fungi suspension was taken out of each of the test tubes as a sample. Each sample was cultured using 20 mL of Glucose Peptone agar medium, and was measured of its viable cell count per 1 mL by plate dilution method. On the basis of the obtained value, the viable cell count per 1 mL of each fungi suspension was calculated. Then, an amount of reduction of the fungi was calculated in logarithm according to the following equation:

Log reduction=log(the viable cell count per 1 mL of each fungi suspension immediately after preparation)−(the viable cell count per 1 mL of each fungi suspension after treatment by each contact lens solution specimen)

The results are indicated in the following TABLE 3.

On the basis of the log reduction calculated as described above, each of the solution specimens was evaluated of its germicidal efficacy. The results of evaluation are also indicated in TABLE 3. The evaluation was carried out based on the First Criteria (relating to sterilization) in ISO 14729. In TABLE 3, "○" indicates that the solution specimen satisfies the First Criteria while "X" indicates that the solution specimen does not satisfy the First Criteria.

TABLE 3

| Specimens | Log reduction | Evaluation of germicidal efficacy |
|---|---|---|
| 1 | 2.09 | ○ |
| 2 | 2.88 | ○ |
| 3 | 2.68 | ○ |
| 4 | 2.84 | ○ |
| 5 | 2.45 | ○ |
| 6 | 2.61 | ○ |
| 7 | 3.04 | ○ |
| 8 | 3.19 | ○ |
| 9 | 2.58 | ○ |
| 10 | 2.45 | ○ |
| 11 | 2.84 | ○ |
| 12 | 2.12 | ○ |
| 13 | 2.53 | ○ |
| 14 | 1.47* | ○ |

*The fungi suspension was kept at 23° C. for four hours.

As is apparent from the results indicated in TABLE 3, the solution specimens Nos. 1–14 exhibited excellent germicidal efficacy, which specimens did not include the sodium chloride and the phosphate, and which included, as the tonicity agent, at least one Component B having an isoelectric point of not lower than 4 and a molecular weight of not smaller than 89. In particular, the solution specimens Nos. 1–13 exhibited the germicidal efficacy in a relatively short period of time (i.e., one hour), <Example 2>

Initially, there were prepared contact lens solution specimens Nos. 15 and 16 by adding, to a predetermined amount of distilled water, a germicidal component (Component A), at least one amino-acid-based component (Component B) selected from the group consisting of selected amino acids, salts of the amino acids, and derivatives of the amino acids, and various additives, so as to have respective different compositions as indicated in the following TABLE 4. Each of the solution specimens has an osmotic pressure of about 290 mOsm/kg and a pH of about 7.3. As the Component A, polyhexamethylene biguamide (PHMB) was used. As the Component B, arginine (whose isoelectric point is 10.76 and molecular weight is 174.20 and which has a pH of 11.20 and an osmotic pressure of 100 mOsm/kg, as measured in 0.1 mol/L aqueous solution thereof) was used in the solution specimen No. 15 while the lysine hydrochloride as used in the solution specimen No. 12 in EXAMPLE 1 (see TABLE 2) was used in the solution specimen No. 16. As the surfactant, "Poloxamer 407" (available from BASF A.G., Germany) was used. As the chelating agent, EDTA•2Na was used. As the thickener, "HPMC 2910" (available from SHIN-ETSU CHEMICALS, CO., LTD., Japan) was used. As the pH adjusting agent, sodium hydroxide (NaOH) or hydrochloric acid (HCl) was used.

In the same manner as in EXAMPLE 1, the log reduction was obtained for each of the contact lens solution specimens Nos. 15 and 16. On the basis of the obtained log reduction, each of the specimens Nos. 15 and 16 was evaluated of its germicidal efficacy also in the same manner as in EXAMPLE 1. The results are also shown in the following TABLE 4. The solution specimens Nos. 15 and 16 were kept at 23° C. for four hours.

TABLE 4

| Contents (w/w %) | | Specimens | |
|---|---|---|---|
| | | 15 | 16 |
| Component A | PHMB | 0.0001 | 0.0001 |
| Component B | arginine | 2.85 | — |
| | lysine hydrochloride | — | 2.6 |
| Surfactant | Poloxamer 407 | 0.5 | 0.5 |
| Chelating agent | EDTA · 2Na | 0.05 | 0.05 |
| Thickener | HPMC 2910 | 0.15 | 0.15 |
| pH adjusting agent | NaOH/HCL | * | * |
| | PH | 7.3 | 7.3 |
| Osmotic pressure [mOsm/kg] | | 290 | 290 |
| Log reduction | | 1.47 | 1.65 |
| Evaluation of the germicidal efficacy | | ○ | ○ |

* suitable amounts

As is apparent from the results indicated in TABLE 4, the contact lens solution specimens Nos. 15 and 16 exhibited excellent germicidal effect.

<Example 3>

Initially, various contact lens solution specimens Nos. 17–21 were prepared by adding, to a predetermined amount of distilled water, a germicidal component (Component A), at least one acidic component (Component C), and various additives, so as to provide respective different compositions as indicated in the following TABLE 5. The pH and the osmotic pressure of each of the solution specimens are also indicated in TABLE 5.

Three kinds of commercially available soft contact lenses ("MENICON FOCUS", "MENICON SOFT MA", AND "MENICON SOFT 72", all available from Menicon Co., Ltd., Japan) were immersed in each of the solution specimens Nos. 17–21 kept at 25° C. In this state, each of the contact lenses was measured of its size (diameter) by a projector (type V12A available from Nikon K.K., Japan), which was set for 20-times magnification (×20). By subtracting the obtained value ($D_1$) indicative of the diameter of each of the immersed soft contact lenses from a nominal value ($D_0$) indicative of the diameter of each of the soft contact lenses before the immersion, there was calculated an amount of change of the size (diameter) for each of the soft contact lenses. The results are indicated in the following TABLE 5.

On the basis of the obtained amounts of change of the size of the soft contact lenses, the solution specimens Nos. 17–21 were evaluated in terms of compatibility with the soft contact lenses, according to the following criteria:

[Criteria for Evaluating the Compatibility of the Solution Specimen with the Soft Contact Lenses]

○: Substantially no size changes were observed in all of the contact lenses immersed in the solution specimen.
Δ: Substantially no size changes were observed in some of the contact lenses immersed in the solution specimen.
X: Considerable size changes were observed in all of the contact lenses immersed in the solution specimen.

TABLE 5

| Contents (w/w %) | | Specimens | | | | |
|---|---|---|---|---|---|---|
| | | 17 | 18 | 19 | 20 | 21 |
| Component A | PHMB | 0.0001 | 0.0001 | 0.0001 | 0.0001 | 0.0001 |
| | glycolic acid | 1.15 | — | — | — | — |
| | lactic acid | — | 1.34 | — | — | — |
| Component C | gluconic acid | — | — | 2.96 | — | — |
| | aspartic acid | — | — | — | 1.94 | — |
| | pyrophosphoric acid | — | — | — | — | 1.54 |
| Surfactant | Poloxamer 407 | 0.5 | 0.5 | 0.5 | 0.5 | 0.5 |
| Chelating agent | EDTA · 2Na | 0.05 | 0.05 | 0.05 | 0.05 | 0.05 |
| Thickener | HPMC 2910 | 0.15 | 0.15 | 0.15 | 0.15 | 0.15 |
| pH adjusting agent | NaOH/HCl | * | * | * | * | * |
| | PH | 7.3 | 7.3 | 7.3 | 7.3 | 7.3 |
| Osmotic pressure [mOsm/kg] | | 290 | 309 | 293 | 281 | 329 |
| Change of size (diameter) of contact lens [mm] | MENICON FOCUS | −0.09 | −0.11 | −0.63 | −0.22 | −0.47 |
| | MENICON SOFT MA | −0.12 | −0.03 | −0.14 | −0.21 | −0.41 |
| | MENICON SOFT 72 | −0.05 | −0.04 | −0.20 | −0.13 | −0.19 |
| Evaluation of compatibility with contact lens | | ○ | ○ | Δ | Δ | Δ |

* suitable amounts

As is apparent from the results indicated in TABLE 5, among the contact lens solution specimens Nos. 17–21 which contained the acidic component (Component C), the solution specimen Nos. 17 and 18 exhibited suitable compatibility with all of the soft contact lenses immersed therein, while the solution specimen Nos. 19–21 exhibited suitable compatibility with some of the soft contact lenses immersed therein.

<Example 4>

Initially, there were prepared contact lens solution specimens Nos. 22–33 by adding, to a predetermined amount of distilled water, a germicidal component (Component A), at least one amino-acid-based component (Component B) selected from the group consisting of selected amino acids, salts of the amino acids, and derivatives of the amino acids, at least one acidic compound (Component C'), and various additives, so as to provide respective different compositions as indicated in the following TABLE 6 and TABLE 7. The pH and the osmotic pressure of each of the solution specimens are also indicated in TABLE 6 and TABLE 7.

In the same manner as in EXAMPLE 1, the log reduction was obtained for each of the contact lens solution specimens Nos. 22–33. On the basis of the obtained log reduction, each of the specimens Nos. 22–33 was evaluated of its germicidal efficacy also in the same manner as in EXAMPLE 1. The results are also shown in the following TABLE 6 and TABLE 7. These solution specimens were kept at 23° C. for four hours.

In the same manner as in EXAMPLE 3, the soft contact lenses were immersed in each solution specimen kept at 25° C., and the size (diameter) was measured for each contact lens. Further, the amount of change of the size was calculated for each of the contact lenses. In the same manner as in EXAMPLE 3, each solution specimen was evaluated in terms of compatibility with the soft contact lenses. The results of evaluation are indicated in TABLE 6 and TABLE 7.

TABLE 6

| Contents (w/w %) | | Specimens | | | | | |
|---|---|---|---|---|---|---|---|
| | | 22 | 23 | 24 | 25 | 26 | 27 |
| Component A | PHMB | 0.0001 | 0.0001 | 0.0001 | 0.0001 | 0.0001 | 0.0001 |
| Component B | arginine | 2.85 | 2.85 | 2.85 | 1.85 | — | 3.43 |
| | lysine hydrochloride | — | — | — | — | 1.91 | — |
| Component C' | glycolic acid | 0.3 | 0.5 | 0.7 | 0.5 | 0.3 | — |
| | citric acid | — | — | — | — | — | 0.5 |
| Component D | glycerin | — | — | — | 0.8 | — | — |
| Surfactant | Poloxamer 407 | 0.5 | 0.5 | 0.5 | 0.5 | 0.5 | 0.5 |
| Chelating agent | EDTA · 2Na | 0.05 | 0.05 | 0.05 | 0.05 | 0.05 | 0.05 |
| Thickener | HPMC 2910 | 0.15 | 0.15 | 0.15 | 0.15 | 0.15 | 0.15 |
| pH adjusting agent | NaOH/HCl | * | * | * | * | * | * |
| PH | | 7.3 | 7.3 | 7.3 | 7.3 | 7.3 | 7.3 |
| Osmotic pressure [mOsm/kg] | | 294 | 292 | 299 | 290 | 290 | 284 |
| Log reduction | | 1.32 | 1.48 | 1.44 | 1.66 | 1.10 | 1.46 |
| Evaluation of the germicidal efficacy | | ○ | ○ | ○ | ○ | ○ | ○ |
| Change of size (diameter) of contact lens [mm] | MENICON FOCUS | 0.06 | 0.04 | 0.01 | 0.16 | 0.16 | 0.05 |
| | MENICON SOFT MA | 0.04 | 0.03 | 0.02 | 0.09 | 0.00 | −0.03 |
| | MENICON SOFT 72 | 0.03 | 0.04 | −0.04 | 0.01 | −0.08 | 0.08 |
| Compatibility with contact lens | | ○ | ○ | ○ | ○ | ○ | ○ |

* Suitable amounts

TABLE 7

| Contents (w/w %) | | Specimens | | | | | |
|---|---|---|---|---|---|---|---|
| | | 28 | 29 | 30 | 31 | 32 | 33 |
| Component A | PHMB | 0.0001 | 0.0001 | 0.0001 | 0.0001 | 0.0001 | 0.0001 |
| Component B | arginine | 2.85 | 2.85 | 2.85 | 3.29 | 3.51 | 1.85 |
| Component C' | glycolic acid | — | — | — | — | — | 0.5 |
| | lactic acid | 0.5 | — | — | — | — | — |
| | gluconic acid | — | 0.5 | — | — | — | — |
| | aspartic acid | — | — | 0.5 | — | — | — |
| | pyrophosphoric acid | — | — | — | — | 0.5 | — |
| | phosphoric acid | — | — | — | 0.5 | — | — |
| Component D | glycerin | — | — | — | — | — | 0.8 |
| Surfactant | Poloxamer 407 | 0.5 | 0.5 | 0.5 | 0.5 | 0.5 | 0.5 |
| Chelating agent | EDTA · 2Na | 0.05 | 0.05 | 0.05 | 0.05 | 0.05 | 0.05 |
| Thickener | HPMC 2910 | 0.15 | 0.15 | 0.15 | 0.15 | 0.15 | — |
| pH adjusting agent | NaOH/HCl | * | * | * | * | * | * |

TABLE 7-continued

| Contents (w/w %) | | Specimens | | | | | |
|---|---|---|---|---|---|---|---|
| | | 28 | 29 | 30 | 31 | 32 | 33 |
| pH | | 7.3 | 7.3 | 7.3 | 7.3 | 7.3 | 7.3 |
| Osmotic pressure [mOsm/kg] | | 302 | 293 | 296 | 286 | 280 | 290 |
| Log reduction | | 1.94 | 2.16 | 1.87 | 1.70 | 1.74 | 1.85 |
| Evaluation of the germicidal efficacy | | ○ | ○ | ○ | ○ | ○ | ○ |
| Change of size (diameter) of contact lens [mm] | MENICON FOCUS | 0.08 | 0.14 | 0.08 | 0.03 | 0.03 | 0.16 |
| | MENICON SOFT MA | 0.06 | 0.08 | 0.04 | −0.07 | −0.10 | 0.08 |
| | MENICON SOFT 72 | 0.08 | 0.05 | 0.05 | 0.02 | 0.03 | 0.00 |
| Compatibility with contact lens | | ○ | ○ | ○ | ○ | ○ | ○ |

As is apparent from the results indicated in TABLE 6 and TABLE 7, the contact lens solution specimens Nos. 22–33 which contained the Component A, the Component B and the Component C' exhibited excellent germicidal efficacy and excellent compatibility with the contact lenses.

<Example 5>

Initially, various contact lens solution specimens Nos. 34–37 were prepared by adding, to a predetermined amount of distilled water, various components in respective amounts as indicated in the following TABLE 8, so as to provide respective different compositions. The pH and the osmotic pressure of each of the prepared solution specimens are also indicated in TABLE 8.

Commercially available soft contact lenses ("MENICON SOFT 72" available from Menicon Co., Ltd., Japan) were immersed in each of the solution specimens Nos. 34–37 for four hours. Thereafter, the contact lenses were taken out of the solution specimens, and directly worn on the eyes of predetermined numbers of subjects indicated in TABLE 8, without being rinsed. Each solution specimen was evaluated by the subjects according to the points rating. By obtaining an average value of the points given by the subjects, each solution specimen was evaluated in terms of eye irritation. In the following TABLE 8, the calculated average value is shown for each solution specimen. The smaller the average value, the smaller the degree of eye irritation as felt by the subjects.

| [Criteria for evaluation in terms of eye irritation] | Point |
|---|---|
| No eye irritation | 0 |
| Very slight eye irritation | 1 |
| Slight eye irritation | 2 |
| Heavy eye irritation | 3 |
| Very heavy eye irritation | 4 |

TABLE 8

| Contents (w/w %) | | Specimens | | | |
|---|---|---|---|---|---|
| | | 34 | 35 | 36 | 37 |
| Component A | PHMB | 0.0001 | 0.0001 | 0.0001 | 0.0001 |
| Component B | arginine | 1.85 | 1.85 | 1.85 | 2.85 |
| Component C' | glycolic acid | 0.5 | 0.5 | 0.5 | — |
| Component D | glycerin | 1 | 1 | 1 | — |
| Surfactant | Poloxamer 407 | 0.5 | 0.5 | 0.5 | 0.5 |
| Chelating agent | EDTA·2Na | 0.055 | 0.055 | 0.055 | 0.055 |
| Thickener | HPMC 2910 | 0.15 | 0.15 | 0.15 | 0.15 |
| pH adjusting agent | NaOH/HCl | * | * | * | * |
| PH | | 7.53 | 7.08 | 6.60 | 7.48 |
| Osmotic pressure [mOsm/kg] | | 291 | 290 | 292 | 286 |
| Number of subjects | | 11 | 20 | 14 | 9 |
| Evaluation of eye irritation (average value) | | 0.1 | 0.3 | 0.9 | 0.4 |

* suitable amounts

As is apparent from the results indicated in the above TABLE 8, the average values were less than 1 in all of the contact lens solution specimens Nos. 34–37. Accordingly, it was confirmed that these solution specimens did not cause undesirable eye irritation. Further, a comparison between the specimen No. 34 and the specimen No. 37 whose pH values are substantially equal to each other revealed that the degree of eye irritation as felt by the subjects was smaller in the specimen No. 34 which contained the glycerin (Component D) than the specimen No. 37 without containing the glycerin.

For comparison, the evaluation in terms of eye irritation was carried out by five subjects for two commercially available contact lens solutions, namely, "ReNu MultiPlus" (available from Bausch & Lomb Incorporated, USA) and "Opti-Free Express" (available from Alcon Laboratories, Inc., USA). The pH values of the solutions were adjusted to 6.5 and 6.48, respectively, by using HCl or NaOH. In the same manner as in EXAMPLE 5, the comparative solutions were evaluated in terms of eye irritation by the subjects. The average values were 2.0 and 3.0, respectively. Thus, it was confirmed that the degree of eye irritation as felt by the subjects was smaller in the contact lens solution specimens Nos. 34–37 according to the present invention than the above-indicated two commercially available solutions as comparative examples.

<Example 6>

Various contact lens solution specimens Nos. 38–43 were prepared by adding, to a predetermined amount of distilled water, various components in respective different amounts, so as to have respective compositions as indicated in the following TABLE 10. The pH and the osmotic pressure of each solution specimen are also indicated in TABLE 10.

Commercially available soft contact lenses ("MENICON SOFT 72" available from Menicon, Co., Ltd., Japan) were immersed in each solution specimen for one hour. Thereafter, the contact lenses were taken out of the solution specimens, and worn, without being rinsed, on the eyes of subjects for not less than two hours, which subjects are free from the staining of the corneas with the fluorescein. After the contact lenses have been removed from the eyes of each subject, the corneas of each subject were inspected for the staining with the fluorescein. The corneas of each subject were observed by using a slit-lamp microscope. Depending upon the degree of staining of the cornea, the degree of the eye trouble was classified into five grades (G0–G4) as indicated in the following TABLE 9, and each contact lens solution was evaluated in terms of the eye trouble. The results of evaluation are indicated in TABLE 10.

TABLE 9

| Grade | Degree of eye trouble | Clinical diagnosis |
|---|---|---|
| G0 | no eye trouble | No clinical treatment is necessary. |
| G1 | very light | Clinical treatment boundary |
| G2 | light | Clinical treatment is sometimes necessary. |
| G3 | medium | Clinical treatment is generally necessary. |
| G4 | serious | Clinical treatment is absolutely necessary. |

For comparison, there was prepared a comparative solution which was the same as the solution specimen No. 38, except that sodium chloride was included in an amount of 0.9 wt. %, in place of arginine and the glycolic acid used in the specimen No. 38. In the same manner as in EXAMPLE 6, the comparative solution was evaluated in terms of the eye trouble. According to the evaluation, two eyes were classified as the grade G1, six eyes were classified as the grade G2, and two eyes were classified as the grade G3.

As is apparent from the results indicated in TABLE 10, the contact lens solution specimens Nos. 38–43 according to the present invention did not cause serious eye trouble in contrast with the above-described comparative solution which contained the sodium chloride as the tonicity adjusting agent. It was further confirmed from the results that the addition of glycolic acid (Component C or C') was effective to prevent the eye trouble, for thereby assuring a significantly high degree of safety.

As is apparent from the foregoing description, in the present ophthalmic solution according to the first embodiment described above, the concentrations of the sodium chloride and the phosphate are made zero or minimized, and at least one germicidal/preservative component selected from the group consisting of the biguamides and the quaternary ammonium salts is included. Further, the present ophthalmic solution includes, in place of the sodium chloride, at least one amino-acid-based component as the tonicity adjusting agent selected from the group consisting of the amino acids each having an isoelectric point of not smaller than 4 and a molecular weight of not smaller than 89, the salts of the amino acids, and the derivatives of the amino acids. Accordingly, the biguamide germicide or the quaternary ammonium salt germicide exhibits its germicidal activity with significantly high efficiency, so that the present ophthalmic solution advantageously provides a considerably high degree of germicidal or preservative effect even if the concentration of the germicidal component in the ophthalmic solution is made low. Thus, the present ophthalmic solution assures enhanced degree of safety to the living subject.

In the contact lens solution according to the second embodiment described above, at least one germicidal/preservative component selected from the group consisting of the biguamides and the quaternary ammonium salts is included, and the concentration of the sodium chloride which inhibits the germicidal efficacy of the germicidal/preservative component is made zero or minimized. Further, at least one acidic component selected from the group consisting of glycolic acid, lactic acid, gluconic acid, aspartic acid, glutamic acid, and pyrophosphoric acid is included as the tonicity adjusting agent, in place of the conventionally used sodium chloride. Accordingly, the germicidal efficacy

TABLE 10

| Contents (w/w %) | | Specimens | | | | | |
|---|---|---|---|---|---|---|---|
| | | 38 | 39 | 40 | 41 | 42 | 43 |
| Component A | PHMB | 0.0001 | 0.0001 | 0.0001 | 0.0001 | 0.0001 | 0.0001 |
| Component B | arginine | 1.85 | 1.85 | — | 2.85 | 2.85 | — |
| Component C (Component C') | glycolic acid | 0.5 | — | 0.76 | 0.5 | — | 1.1 |
| Component D | glycerin | 0.8 | 0.8 | 0.8 | — | — | — |
| Surfactant | Poloxamer 407 | 0.5 | 0.5 | 0.5 | 0.5 | 0.5 | 0.5 |
| Chelating agent | EDTA · 2Na | 0.05 | 0.05 | 0.05 | 0.05 | 0.05 | 0.05 |
| pH adjusting agent | NaOH/HCl | * | * | * | * | * | * |
| pH | | 7.3 | 7.3 | 7.3 | 7.3 | 7.3 | 7.3 |
| Osmotic pressure [mOsm/kg] | | 286 | 285 | 290 | 289 | 292 | 286 |
| Evaluation in terms of eye trouble by grading [number of eyes] | G0 | 20 | 2 | 8 | 20 | 2 | 9 |
| | G1 | 0 | 5 | 2 | 0 | 4 | 1 |
| | G2 | 0 | 3 | 0 | 0 | 3 | 0 |
| | G3 | 0 | 0 | 0 | 0 | 1 | 0 |
| | G4 | 0 | 0 | 0 | 0 | 0 | 0 |

* suitable amounts of the germicidal or preservative component is prevented from being deteriorated, and the adsorption of the germicidal or preservative component on the contact lens is effectively prevented owing to the presence of the at least one acidic component described above. Therefore, the present contact lens solution assures a significantly high degree of safety without causing undesirable eye trouble such as the inflammation of the eye and the staining of cornea over the substantially entire surface with the fluorescein.

In the contact lens solution according to the third embodiment described above, at least one germicidal/preservative component selected from the group consisting of the biguamides and the quaternary ammonium salts is included, and the concentration of the sodium chloride which inhibits the germicidal efficacy of the germicidal/preservative component is made zero or minimized. Further, at least one amino-acid-based component selected from the group consisting of the amino acids each having an isoelectric point of not smaller than 4 and a molecular weight of not smaller than 89, the salts of the amino acids, and the derivatives of the amino acids is used in combination with the at least one acidic compound which has at least one carboxyl group or at least one phosphoric acid group and which does not generate metal ions in an aqueous solution thereof. Namely, the at least one amino-acid-based component and the at least one acidic compound are used in combination as the tonicity adjusting agent in place of the conventionally used sodium chloride. Therefore, the present contact lens solution assures excellent compatibility with the contact lens while effectively avoiding an undesirable change of the size of the contact lens due to swelling or shrinkage. Further, the present contact lens solution enjoys the advantages provided by the amino-acid-based component and the acidic compound. Namely, even if the concentration of the germicidal/preservative component is low, the contact lens solution exhibits the germicidal effect with significantly high efficiency while avoiding the adsorption of the germicidal component on the contact lens. Thus, the present contact lens solution assures a sufficiently high degree of safety without causing any eye trouble such as the inflammation of the eye and the staining of the cornea over the substantially entire surface with the fluorescein.

What is claimed is:

1. An ophthalmic solution which comprises at least one germicidal/preservative component selected from the group consisting of biguanides and quaternary ammonium salts, further comprising;
   at least one amino-acid-based component selected from the group consisting of amino acids each having an isoelectric point of not smaller than 4 and a molecular weight of not smaller than 89, salts of said amino acids, and derivatives of said amino acids;
   at least one acidic component selected from the group consisting of glycolic acid, lactic acid, gluconic acid, aspartic acid, glutamic acid, and pyrophosphoric acid;
   sodium chloride, the concentration of which in said ophthalmic solution is adjusted to be held in a range of 0–0.2 wt. %; and
   phosphate, a concentration of which in said ophthalmic solution is adjusted to be held in a range of 0–0.5 wt. %.

2. An ophthalmic solution according to claim 1, wherein said isoelectric point of said at least one amino-acid-based component is not smaller than 5.

3. An ophthalmic solution according to claim 1, wherein said at least one amino-acid-based component is neutral or basic.

4. An ophthalmic solution according to claim 1, wherein said at least one amino-acid-based component includes, in its one molecule, at least one acidic group which derives from carboxylic acid or sulfuric acid, and at least one basic group which derives from amino group or imino group.

5. An ophthalmic solution according to claim 4, wherein a ratio of said at least one acidic group to said at least one basic group is held in a range of 1:1–1:4.

6. An ophthalmic solution according to claim 1, wherein said amino acids are γ-aminobutyric acid, alanine, cysteine, serine, taurine, threonine, valine, histidine, 4-hydroxyproline, phenylalanine, proline, and ε-aminocaproic acid.

7. An ophthalmic solution according to claim 1, wherein said amino acids are lysine and arginine.

8. An ophthalmic solution according to claim 1, further including glycerin.

9. An ophthalmic solution according to claim 1, wherein said at least one amino-acid-based component has an osmotic pressure of not lower than 50 mOsm/kg in 0.1 mol/L aqueous solution thereof.

10. An ophthalmic solution for a contact lens according to claim 1.

11. An ophthalmic solution for a soft contact lens according to claim 1.

12. A solution according to claim 1, wherein a said at least one acidic component has a concentration held in a range of 0.001–5 wt. %.

13. A solution according to claim 1, wherein said at least one germicidal/preservative component has a concentration held in a range of 0.000001–0.3 wt. %.

14. A solution according to claim 1, having a pH in a range of 6–8.

15. A solution for a contact lens which comprises at least one germicidal/preservative component selected from the group consisting of biguanides and quaternary ammonium salts, further comprising;
   at least one amino-acid-based component selected from the group consisting of amino acids each having an isoelectric point of not smaller than 4 and a molecular weight of not smaller than 89, salts of said amino acids, and derivatives of said amino acids;
   at least one acidic component selected from the group consisting of glycolic acid, citric acid, lactic acid, gluconic acid, aspartic acid, glutamic acid, phosphoric acid, and pyrophosphoric acid; and
   sodium chloride, the concentration of which in said ophthalmic solution is adjusted to be held in a range of 0–0.2 wt. %.

16. A solution according to claim 15, wherein said at least one acidic compound has a concentration held in a range of 0.001–5 wt. %.

17. A solution according to claim 15, further including glycerin.

18. A solution according to claim 15, wherein said at least one germicidal/preservative component has a concentration held in a range of 0.000001–0.3 wt. %.

19. A solution according to claim 15, wherein said at least one amino-acid-based component has a concentration held in a range of 0.01–5 wt. %.

20. A solution according to claim 15, wherein said at least one amino-acid-based component has an osmotic pressure of not lower than 50 mOsm/kg in 0.1 mol/L aqueous solution thereof.

21. A solution according to claim 15, having a pH in a range of 6–8.

* * * * *